United States Patent
Namikawa et al.

(10) Patent No.: US 11,513,101 B2
(45) Date of Patent: Nov. 29, 2022

(54) ELASTIC MATRIX DETERMINATION METHOD AND VIBRATION ANALYSIS METHOD FOR LAMINATED IRON CORE

(71) Applicant: JFE STEEL CORPORATION, Tokyo (JP)

(72) Inventors: Misao Namikawa, Tokyo (JP); Gou Kijima, Tokyo (JP)

(73) Assignee: JFE STEEL CORPORATION, Tokyo (JP)

(*) Notice: Subject to any disclaimer, the term of this patent is extended or adjusted under 35 U.S.C. 154(b) by 57 days.

(21) Appl. No.: 16/960,931

(22) PCT Filed: Jan. 21, 2019

(86) PCT No.: PCT/JP2019/001704
§ 371 (c)(1),
(2) Date: Jul. 9, 2020

(87) PCT Pub. No.: WO2019/146554
PCT Pub. Date: Aug. 1, 2019

(65) Prior Publication Data
US 2020/0340952 A1 Oct. 29, 2020

(30) Foreign Application Priority Data
Jan. 24, 2018 (JP) .............. JP2018-009662

(51) Int. Cl.
*G01N 33/204* (2019.01)
*G01N 29/12* (2006.01)

(52) U.S. Cl.
CPC ........... *G01N 29/12* (2013.01); *G01N 33/204* (2019.01); *G01N 2291/014* (2013.01); *G01N 2291/0231* (2013.01); *G01N 2291/0234* (2013.01); *G01N 2291/0289* (2013.01); *G01N 2291/02827* (2013.01); *G01N 2291/26* (2013.01)

(58) Field of Classification Search
CPC .. G06F 30/23; G06F 2119/14; G06F 2111/10; G01N 29/12; G01N 33/204; G01N 2291/26; G01N 2291/02827; G01N 2291/0289; G01N 2291/0234; G01N 2291/014; G01N 2291/0231; H01F 27/245; H01F 27/33; H01F 41/0233; H01F 1/16

USPC .............................................. 73/645
See application file for complete search history.

(56) References Cited

U.S. PATENT DOCUMENTS

| | | | | |
|---|---|---|---|---|
| 3,943,755 A * | 3/1976 | Arii | ................. | G01N 29/07 73/597 |
| 4,499,770 A * | 2/1985 | Kriz | ................. | G01N 29/11 73/599 |
| 4,749,891 A * | 6/1988 | Sheng | ................. | B07B 1/42 310/15 |
| 5,626,944 A * | 5/1997 | Rasmussen | ........ | B29C 59/046 425/374 |
| 2003/0222871 A1* | 12/2003 | Brombolich | ........ | G06F 30/23 345/427 |
| 2015/0043787 A1* | 2/2015 | Fredrich | ........... | G06T 7/136 382/109 |
| 2021/0404992 A1* | 12/2021 | Namikawa | ......... | G01N 29/223 |

FOREIGN PATENT DOCUMENTS

| | | | |
|---|---|---|---|
| CN | 104359549 B | | 7/2015 |
| JP | 2008036671 | * | 2/2008 |
| JP | 2014-071689 A | | 4/2014 |
| JP | 2015032295 | * | 2/2015 |
| WO | WO2015182891 | * | 2/2015 |
| WO | WO-2016027874 A1 | * | 2/2016 ........... G01B 11/168 |

OTHER PUBLICATIONS

Feb. 19, 2021 Extended European Search Report issued in European Patent Application No. 19743839.3.
Jul. 4, 2022 European Office Action issued in European Patent Application No. 19743839.3.

* cited by examiner

*Primary Examiner* — Jacques M Saint Surin
(74) *Attorney, Agent, or Firm* — Oliff PLC (57) ABSTRACT

An elastic matrix determination method and a vibration analysis method for a laminated iron core, with which it is possible to optimally determine an elastic modulus of a laminated iron core. When a vibration analysis of a laminated iron core obtained by laminating steel sheets is performed by using a configuration expression indicating a relationship between stress and strain in a matrix display by using an elastic matrix, a shear modulus in two surfaces including a laminating direction of the laminated iron core included in the elastic matrix in the configuration expression is determined in consideration of slip between laminated steel sheets.

12 Claims, 6 Drawing Sheets

ELASTIC MATRIX DETERMINATION METHOD AND VIBRATION ANALYSIS METHOD FOR LAMINATED IRON CORE

TECHNICAL FIELD

The present invention relates to an elastic matrix determination method and a vibration analysis method in a configuration expression indicating a relationship between stress and strain in elastic deformation of an iron core applied when a vibration analysis of the laminated iron core such as a transformer iron core is performed.

BACKGROUND ART

A transformer such as a power distribution transformer is configured by winding coils around a laminated iron core in which electrical steel sheets are laminated. Performance that is important as the transformer includes iron loss (no-load loss) characteristics, magnetostrictive current characteristics, noise characteristics, and the like.

The power distribution transformer is installed in various places. Particularly, the transformer installed in an urban area is strongly required to have low noise. Thus, in recent years, in particular, the noise characteristics have become increasingly important in consideration of a surrounding environment where the transformer is installed.

A grain orientated electrical steel sheet is often used as an iron core material of the transformer. The grain orientated electrical steel sheet has material expansion and contraction due to excitation called magnetostriction, and the magnetostrictive vibration under excitation is said to be a main cause of transformer noise. Therefore, the transformer noise performance is considered to strongly depend in the magnetostriction performance of the electrical steel sheet to be used, and when a low-noise transformer is manufactured, the electrical steel sheet having the low magnetostriction characteristics is used as an iron core material.

However, despite the fact that the iron core is manufactured by actually using the electrical steel sheet having excellent magnetostriction performance, there are many cases where sufficient transformer low noise characteristics cannot be obtained. When a cause of such an occurrence is investigated, there are many cases considered to be a resonance phenomenon between a natural frequency of the transformer iron core and a magnetostrictive vibration of the electrical steel sheet. Therefore, it is extremely important to calculate and predict mechanical vibration characteristics including the natural vibration of the transformer iron core in designing and manufacturing the transformer.

Therefore, an analysis device and an analysis method are proposed in which a nodal force of each node of the finite element or equivalent to a strain of each finite element according to a magnetic flux density given to an electrical component based on a numerical analysis model expressed in a combination of a plurality of finite elements in a finite element analysis having an electrical component including a magnetic material in which the magnetostriction occurs (for example, see PTL 1).

CITATION LIST

Patent Literature

PTL 1: JP 2014-71689 A

SUMMARY OF INVENTION

Technical Problem

However, the related art described in PTL 1 described above uses a governing expression of a structural analysis configured of an equilibrium of force, a configuration expression illustrating a relation between stress and strain, and a relational expression of displacement and strain to perform a quasi static structural analysis.

Of these, a configuration expression illustrating a relationship between a stress tensor $\{\sigma\}$ and a strain tensor $\{\varepsilon\}$ is represented by $\{\sigma\}=\{D\}\{\varepsilon\}$ ({ } indicates a tensor).

Here, $\{D\}$ is a tensor representing the relationship between strain and stress. When components are displayed, it becomes like the expression (1).

[Math. 1]

$$\sigma_{ij} = \sum_k \sum_l D_{ijkl} \cdot \varepsilon_{kl} \qquad (1)$$

In the expression, $\{D\}$ has 81 components, and $\{\sigma\}$ and $\{\varepsilon\}$ each have 9 components. Here, since the tensor as a physical quantity is a symmetric tensor, independent components of $\{\sigma\}$ and $\{\varepsilon\}$ are respectively 6 components. Therefore, the configuration expression is represented by the following matrix.

$[\sigma]=[D][\varepsilon]$ ([ ] indicates a matrix. [D] is called an elastic matrix.)

When the components are displayed, a result is as illustrated in expression (2).

[Math. 2]

$$\begin{bmatrix} \sigma_{xy} \\ \sigma_{yy} \\ \sigma_{zz} \\ \sigma_{yz} \\ \sigma_{zx} \\ \sigma_{xy} \end{bmatrix} = [D_{ij}] \begin{bmatrix} \varepsilon_{xy} \\ \varepsilon_{yy} \\ \varepsilon_{zz} \\ \varepsilon_{yz} \\ \varepsilon_{zx} \\ \varepsilon_{xy} \end{bmatrix} \qquad (2)$$

A relationship between a vertical stress $\sigma_i$ and a vertical strain $\varepsilon_i$ is expressed by using the elastic matrix [D], and a relationship between a shear strain $\tau_{ij}$ and a shear strain $\gamma_{ij}$ is expressed by using a modulus of rigidity G.

However, in the related art described above, there is no description about setting of the elastic matrix [D] or the modulus of rigidity G, and there is no description on how to determine the elastic matrix [D] or the modulus of rigidity G. However, in general, the elastic modulus of a member such as the electrical steel sheet constituting the electrical component to be subjected to structural analysis is often applied as it is.

In this case, when a mechanical vibration calculation result of the electrical component to be subjected to the structural analysis is compared with a result of an actual measurement of the mechanical vibration, it is known that there is a large difference between a calculated value and the actual measurement value.

In order to suppress the difference between the calculated value and the actual measurement value, it is necessary to make a prototype of the electrical component to be subjected to the structural analysis and measure the elastic modulus. That is reversing the logical order of things and it is difficult to reflect the structural analysis by a structural analysis program on a design of the electrical component.

Therefore, the present invention has been made in view of the problems described above of the related art, and an object the present invention is to provide an elastic matrix determination method and a vibration analysis method for a laminated iron core, with which it is possible to optimally determine an elastic modulus of a laminated iron core.

Solution to Problem

In order to solve the above problems, the gist of the present invention is as follows.

[1] An elastic matrix determination method including: determining, when a vibration analysis of a laminated iron core obtained by laminating steel sheets is performed by using a configuration expression expressing a relationship between stress and strain in a matrix display, a shear modulus in two surfaces including a laminating direction of the laminated iron core included in an elasticity matrix in the configuration expression, in consideration of slip between laminated steel sheets.

[2] The elastic matrix determination method according to [1], further including: creating an iron core for testing obtained by laminating steel sheets; measuring an actual measurement value of a natural frequency by vibrating the created iron core for testing in a laminating direction; estimating, in consideration of slip between the laminated steel sheets, a relationship between the shear modulus and the natural frequency by performing a structural analysis plurality times by taking, as a parameter, the shear modulus for the iron core for testing; and determining the shear modulus from a relationship between the shear modulus and the natural frequency estimated by using the actual measurement value of the natural frequency.

[3] The elastic matrix determination method according to [1], further including: forming an iron core for testing obtained by laminating steel sheets, and measuring an actual measurement value of a natural frequency by vibrating the iron core for testing in a laminating direction; measuring, in consideration of slip between the laminated steel sheets, a relationship between the shear modulus, an elastic modulus, and the natural frequency by performing a structural analysis plurality times, by taking, as individual parameters, the shear modulus and the elastic modulus, for the iron core for testing; and determining the shear modulus and the elastic modulus from a relationship between the shear modulus, the elastic modulus, and the natural frequency measured by using the actual measurement value of the natural frequency.

[4] The elastic matrix determination method according to any one of [1] to [3], in which the laminated iron core is configured by laminating a plurality of electrical steel sheets.

[5] The elastic matrix determination method according to [4], in which the laminated iron core is a laminated iron core for a transformer.

[6] A vibration analysis method for a laminated iron core including: performing a vibration analysis of a laminated iron core obtained by laminating steel sheets by incorporating a shear modulus determined by the elastic matrix determination method according to any one of [1] or [2] into an elastic matrix of a configuration expression in which a relationship between stress and strain is expressed by a tensor display using a response function.

[7] A vibration analysis method for a laminated iron core including: performing a vibration analysis of a laminated iron core obtained by laminating steel sheets by incorporating a shear modulus and an elastic modulus determined by the elastic matrix determination method according to [3] into an elastic matrix of a configuration expression in which a relationship between stress and strain is expressed by a tensor display using a response function.

[8] The vibration analysis method for a laminated iron core according to [6] or [7], in which the laminated iron core is an iron core for a transformer, obtained by laminating a plurality of electrical steel sheets.

Advantageous Effects of Invention

According to the elastic matrix determination method for a laminated iron core according to the present invention, it is possible to suppress a difference between the actual measurement value and the calculated value of the vibration characteristics by appropriately setting, in consideration of slip between laminated steel sheets, the elastic modulus of the configuration expression in which the relationship between stress and strain is indicated by using the vibration analysis.

In addition, the vibration analysis method for a laminated iron core according to the present invention can improve an accuracy of the vibration analysis by performing the vibration analysis by incorporating a properly set elastic modulus to the configuration expression.

DESCRIPTION OF EMBODIMENTS

Hereinafter, embodiments of an elastic matrix determination method for a laminated iron core and a vibration analysis method for the laminated iron core according to the present invention will be described with reference to the drawings. The drawings are schematic and may differ from actual ones. In addition, the following embodiments illustrate a device and a method for embodying the technical idea of the present invention, and do not limit the configuration to the following. That is, the technical idea of the present invention can be variously modified within the technical scope described in the claims.

Figure 1:
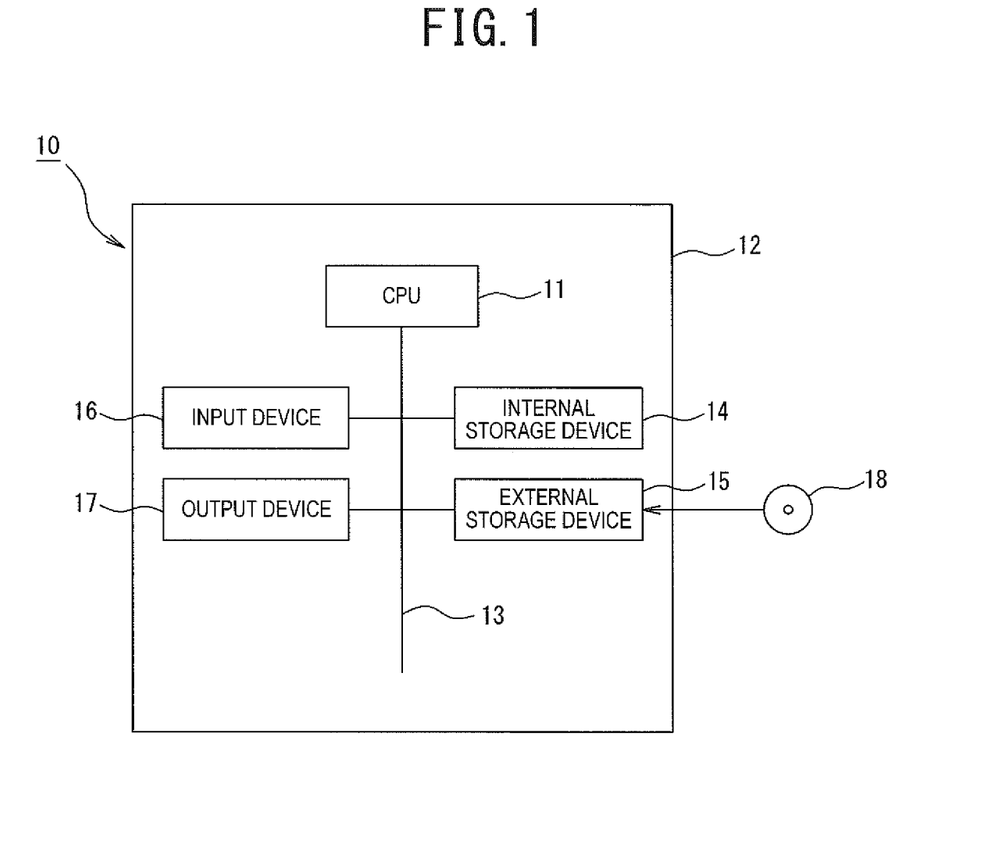
FIG. 1 is a configuration diagram illustrating a vibration analysis device applicable to the present invention.

As illustrated in FIG. 1, the vibration analysis device 10 includes a computation processing device 12 having a CPU 11. The CPU 11 is connected to an internal storage device 14 such as a RAM and a ROM, an external storage device 15, an input device 16 such as a keyboard and a mouse, and an output device 17 for outputting image data to a display via an internal bus 13.

The external storage device 15 includes a readable disk drive such as a hard disk drive or a solid state drive, and a drive device such as a CD, a DVD, or a BD for reading data from a recording medium. A recording medium 18 storing a commercially available vibration analysis program is set in the external storage device 15, and the read vibration analysis program is installed in a disk drive. The installation of the vibration analysis program is not limited to a case where the recording medium 18 is used, and the vibration analysis program may be downloaded via a network.

The CPU 11 performs a vibration analysis by using the finite element method using input data for analysis input according to an installed vibration analysis program, and outputs and displays, on a display, an analysis result such as a natural frequency according to a vibration mode from the output device 17. The analysis result is not limited to being displayed in the display, but can be printed by a printer or transmitted via a network.

Figure 2:
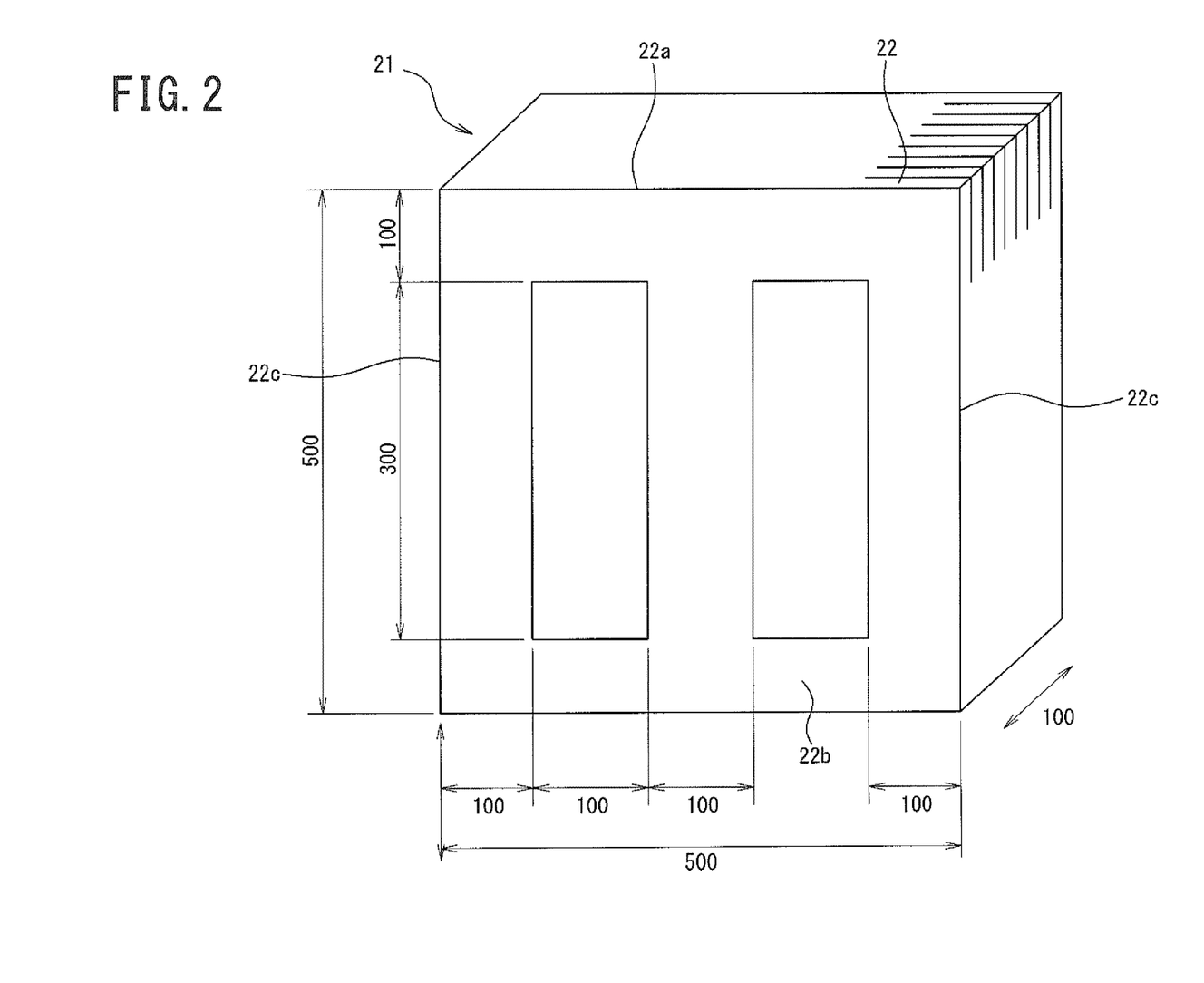
FIG. 2 is a perspective view illustrating an iron core of a 3-phase and 3-leg transformer.
Figure 3A:
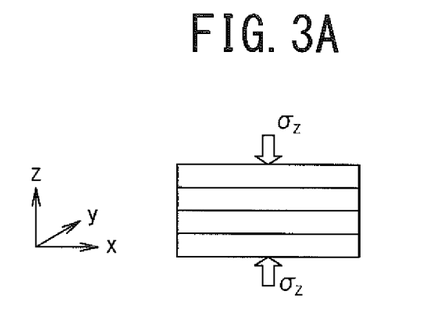
FIGS. 3A, 3B, 3C, and 3D are characteristic diagrams illustrating vertical stress and shear stress.
Figure 3B:
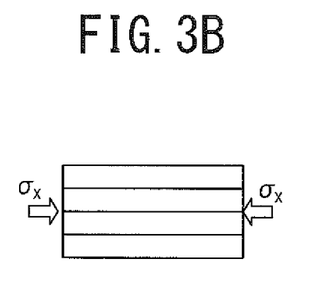
Figure 3C:
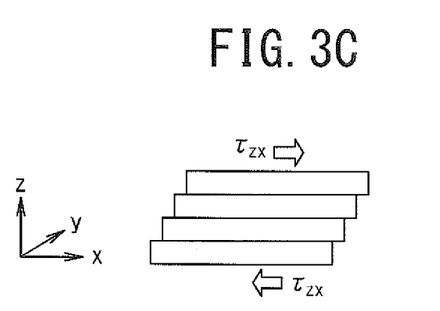
Figure 3D:
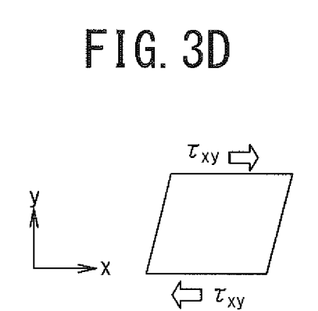

A laminated iron core 21 to be analyzed in the present embodiment is, for example, a laminated iron core for a 3-phase and 3-leg transformer used as a power distribution transformer. As illustrated in FIG. 2, for example, 333 grain orientated electrical steel sheets 22 having a thickness of 0.3 mm and three leg portions 22c connected to each other between an upper yoke 22a and a lower yoke 22b are laminated, and fixed by winding a glass tape.

between stress and strain, which is a governing equation of a structural analysis.

The configuration expression is represented by the following expression (3) when a laminated material is replaced with an equivalent homogeneous body and an influence of the lamination is expressed by a value of the elastic matrix.

$$[\sigma]=[C][\varepsilon] \quad (3)$$

Here, $[\sigma]$ is a stress matrix, $[C]$ is an elastic matrix (stiffness matrix) as a response function, and $[\varepsilon]$ is a strain matrix.

Here, assuming that a laminating direction of the steel sheets is a Z direction, one of a two-dimensional plane orthogonal to the Z direction is an X direction, and the other is a Y direction. As illustrated in FIGS. 3A to 3D, vertical components of the stress matrix $[\sigma]$ are represented by a vertical stress $\sigma x$ in the X direction, a vertical stress $\sigma y$ in the Y direction, and a vertical stress $\sigma z$ in the Z direction, and shear components are represented by a shear stress $\tau zx$ in a ZX plane, a shear stress $\tau yz$ in a YZ plane, and a shear stress $\tau xy$ in an XY plane.

Similarly, vertical components of the strain matrix $[\varepsilon]$ are represented by a vertical strain $\varepsilon x$ in the X direction, a vertical strain $\varepsilon y$ in the Y direction, and a vertical strain $\varepsilon z$ in the Z direction, and shear components are represented by shear strain $\gamma zx$ in the ZX plane, shear strain $\gamma yz$ in the YZ plane, and a shear strain $\gamma xy$ in the XY plane.

The elastic matrix $[C]$ is represented by 36 elastic moduli $C_{ij}$ (i=1 to 6, j=1 to 6).

When these are displayed in a matrix, the following expression (4) is obtained.

[Math. 3]

$$\begin{bmatrix} \sigma_x \\ \sigma_y \\ \sigma_z \\ \hline \tau_{yz} \\ \tau_{zx} \\ \tau_{xy} \end{bmatrix} = \begin{bmatrix} C_{11} & C_{12} & C_{13} & C_{14} & C_{15} & C_{16} \\ C_{12} & C_{22} & C_{23} & C_{24} & C_{25} & C_{26} \\ C_{13} & C_{23} & C_{33} & C_{34} & C_{35} & C_{36} \\ \hline C_{14} & C_{24} & C_{34} & C_{44} & C_{45} & C_{46} \\ C_{15} & C_{25} & C_{35} & C_{45} & C_{55} & C_{56} \\ C_{16} & C_{26} & C_{36} & C_{46} & C_{56} & C_{66} \end{bmatrix} \begin{bmatrix} \varepsilon_x \\ \varepsilon_y \\ \varepsilon_z \\ \hline \gamma_{yz} \\ \gamma_{zx} \\ \gamma_{xy} \end{bmatrix} \begin{array}{l} \text{vertical components} \\ \text{shear components} \end{array} \quad (4)$$

As an example, dimensions of the upper yoke 22a and the lower yoke 22b are set to width of 100 mm×length of 500 mm. Dimensions of the three legs 22c are set to width of 100 mm×length of 300 mm, and the three legs 22c are connected between the upper yoke 22a and the lower yoke 22b at intervals of 100 mm.

When the vibration analysis of the laminated iron core 21 of such a 3-phase and 3-leg transformer is performed, a configuration expression is used illustrating a relationship Since the laminated iron core is manufactured by laminating grain orientated electrical steel sheets, it has the mechanical symmetry of the laminated iron core, and also has 180 degree symmetry in a longitudinal direction of the laminated steel sheet and in a direction perpendicular thereto. Therefore, as an anisotropic classification, an orthotropic anisotropy is provided. Therefore, an object having the orthogonal anisotropy can be basically represented by a total of 9 elastic moduli of $C_{11}$, $C_{12}$, $C_{13}$, $C_{22}$, $C_{23}$, $C_{33}$, $C_{44}$, $C_{55}$, and $C_{66}$ as illustrated in the following expression (5).

[Math. 4]

$$\begin{bmatrix} \sigma_x \\ \sigma_y \\ \sigma_z \\ \hline \tau_{yz} \\ \tau_{zx} \\ \tau_{xy} \end{bmatrix} = \begin{bmatrix} C_{11} & C_{12} & C_{13} & 0 & 0 & 0 \\ C_{12} & C_{22} & C_{23} & 0 & 0 & 0 \\ C_{13} & C_{23} & C_{33} & 0 & 0 & 0 \\ \hline 0 & 0 & 0 & C_{44} & 0 & 0 \\ 0 & 0 & 0 & 0 & C_{55} & 0 \\ 0 & 0 & 0 & 0 & 0 & C_{66} \end{bmatrix} \begin{bmatrix} \varepsilon_x \\ \varepsilon_y \\ \varepsilon_z \\ \hline \gamma_{yz} \\ \gamma_{zx} \\ \gamma_{xy} \end{bmatrix} \begin{array}{l} \text{vertical components} \\ \text{shear components} \end{array} \quad (5)$$

$$C_{11} = \frac{1 - v_{yz}v_{zy}}{E_y E_z \Delta} \tag{6}$$

$$C_{12} = \frac{v_{yx} + v_{zx}V_{yz}}{E_y E_z \Delta} \tag{7}$$

$$C_{13} = \frac{v_{zx} + v_{yx}v_{zy}}{E_y E_z \Delta} \tag{8}$$

$$C_{22} = \frac{1 - v_{xz}v_{zx}}{E_z E_x \Delta} \tag{9}$$

$$C_{23} \frac{v_{zy} + v_{xy}v_{zx}}{E_x E_y \Delta} \tag{10}$$

$$C_{33} = \frac{1 - v_{xy}v_{yx}}{E_x E_y \Delta} \tag{11}$$

$$\Delta = \frac{1 - v_{xy}v_{yx} - v_{xz}v_{zx} - v_{xy}v_{yz} - 2v_{yx}v_{zy}v_{zx}}{E_x E_y E_z} \tag{12}$$

Among them, the elastic moduli $C_{11}$, $C_{12}$, $C_{13}$, $C_{22}$, $C_{23}$, and $C_{33}$ can be calculated by expressions (6) to (12) according to the elastic moduli Ex, Ey, and Ez, and Poisson's ratios vxy, vyx, vyz, vzy, vzx, and vxz.

Here, Ex is the elastic modulus (Young's modulus) in the X direction, Ey is the elastic modulus (Young's modulus) in the Y direction, vxy is the Poisson's ratio in the XY plane, vyx is the Poisson's ratio in the YX plane, and vyz is the Poisson's ratio in the YZ plane, and vzy is the Poisson's ratio in the ZY plane, vzx is the Poisson's ratio in the ZX plane, and vxz is the Poisson's ratio in the XZ plane. The elastic modulus $C_{44}$ is a shear modulus Gyz in the YZ plane, the elastic modulus $C_{55}$ is a shear modulus Gzx in the ZX plane, and the elastic modulus $C_{66}$ is a shear modulus Gxy in the XY plane. The elastic moduli Ex and Ey can be set to be equal to the elastic moduli Ex0 and Ey0 of one steel sheet, but the elastic modulus Ez cannot be set to be substantially equal to the elastic modulus Ez0 of one steel sheet. The reason is that there is a slight gap between the laminated steel sheets.

Also, the shear modulus Gxy in the XY plane can be set equal to the shear modulus Gxy0 of one steel sheet, but the shear modulus Gzx in the ZX plane and the shear modulus Gyz in the YZ plane cannot be set to the shear moduli Gzx0 and Gyz0 of one steel sheet as they are.

The reason is that, in the laminated steel sheet, since slip occurs in the X direction and the Y direction orthogonal to the laminating direction at the interface between the respective laminated steel sheets, an influence of the slip between the steel sheets needs to be reflected in the shear moduli Gzx and Gyz.

Therefore, in the elastic matrix, it is important to determine the elastic modulus Ez, the shear modulus Gzx in the ZX plane, and the shear modulus Gyz in the YZ plane, in the vibration analysis using the relational expression of stress and strain of the laminated iron core.

However, in order to make the shear modulus Gzx in the ZX plane and the shear modulus Gyz in the YZ plane reflect the influence of slip between steel sheets, a laminated iron core for the 3-phase and 3-leg transformer is actually manufactured and an accurate shear moduli Gzx and Gyz have to be measured. However, if the measured natural frequency of the manufactured laminated iron core for the 3-phase and 3-leg transformer does not coincide with a natural frequency to be target, it is necessary to remanufacture the iron core.

It is difficult to manufacture an iron core of which the natural frequency coincides with the natural frequency to be target by repeating the process.

Figure 4:
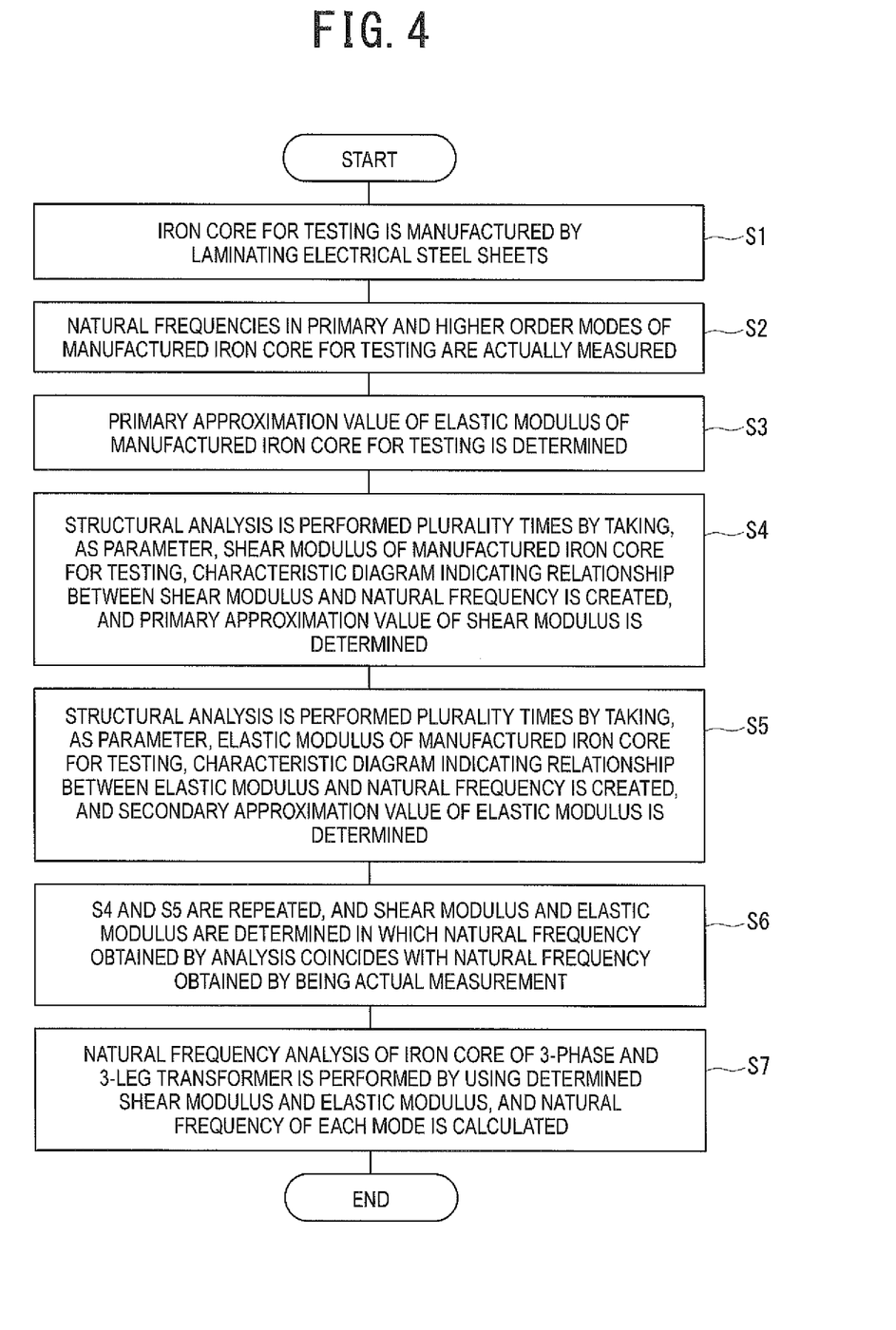
FIG. 4 is a flowchart illustrating a procedure of an elastic modulus determination method in a configuration expression of a laminated iron core.

Thus, in the present embodiment, the elastic matrix determination method is performed according to a procedure illustrated in FIG. 4 to determine, in consideration of the elastic modulus and slip in the laminating direction, the shear modulus between the laminated electrical steel sheets.

To determine the elastic matrix, instead of manufacturing the iron core itself, first, an iron core for testing using a same electrical steel sheet as the iron core is manufactured (step S1). For example, a rectangular parallelepiped iron core for testing is manufactured by laminating, for example, 20 sheets of grain orientated electrical steel sheets each having a thickness of 0.3 mm, a width of 30 mm, and a length of 280 mm and a glass tape is wound thereon to be fixed.

Here, a shape of the iron core for testing is not limited to the rectangular parallelepiped. Not only a rectangular parallelepiped, but also a corner may be rounded, a notch or a cutout may be partially formed, and it may not necessarily be a rectangular parallelepiped. Further, an iron core formed by laminating elliptical electrical steel sheets may be used.

Hereinafter, details of the present invention will be described using the iron core for testing as the rectangular parallelepiped iron core.

Next, an impedance head for measuring an acceleration and a force is attached between the created rectangular parallelepiped iron core for testing and a vibrator, and the natural frequency is measured while the rectangular parallelepiped iron core for testing is supported at a center (step S2). With a vibration direction as the steel sheet laminating direction, the natural frequencies of a primary mode and a higher order mode of a bending vibration at a center support (both ends free) are obtained. In the case of the center support, the higher order mode becomes a third mode.

A support position at this time may be center support (both ends free) or both ends support (center free). Further, one end of the iron core for testing may be fixed and the other end may be free.

Next, natural vibration analysis of the iron core for testing is performed by using structural analysis software installed in the vibration analysis device 10. First, assuming that the elastic modulus Ez is equal to that of one steel sheet used for the iron core for testing, a primary approximation value of the elastic modulus Ez is set to Ez1 (step S3).

Figure 6A:
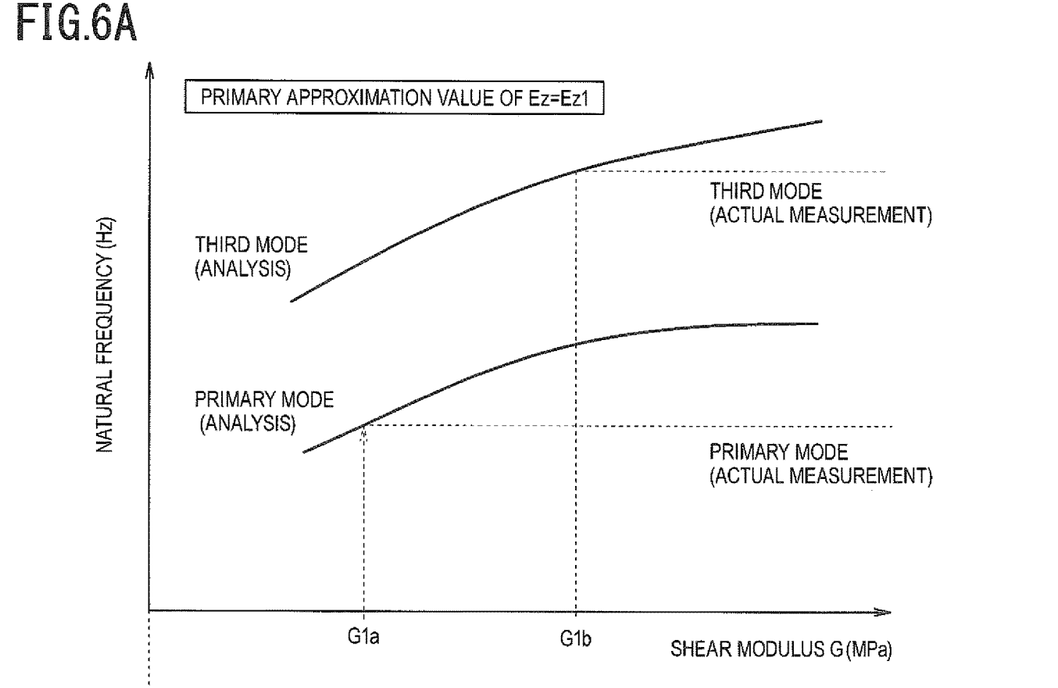
FIGS. 6A and 6B are characteristic diagrams illustrating a relationship between a shear modulus, an elastic modulus, and a natural frequency.

Then, based on a result of performing the structural analysis plurality times while changing a value by taking, as a parameter, the shear modulus G, with the shear modulus Gyz=Gzx=G of the iron core, the relationship between the shear modulus G and the natural frequency is measured, and a characteristic diagram illustrated in FIG. 6A is created.

The characteristic diagram is obtained by making the shear modulus G in a horizontal axis and the natural frequency in a vertical axis. The relationship between the shear modulus G and the natural frequency of the iron core for testing in the primary mode and the third mode in the bending vibration mode at both ends free is illustrated.

Next, the actual measurement values of the natural frequencies of the primary mode and the third mode in the characteristic diagram of FIG. 6A are given, and each shear modulus G is calculated. Therefore, the primary approximation value of the shear modulus G can be determined (step S4).

For example, an average value of the shear moduli G1a and G1b of the primary mode and the third mode can be set to a primary approximation value G1 (G1=(G1a+G1b)/2) of the shear modulus G.

Figure 6B:
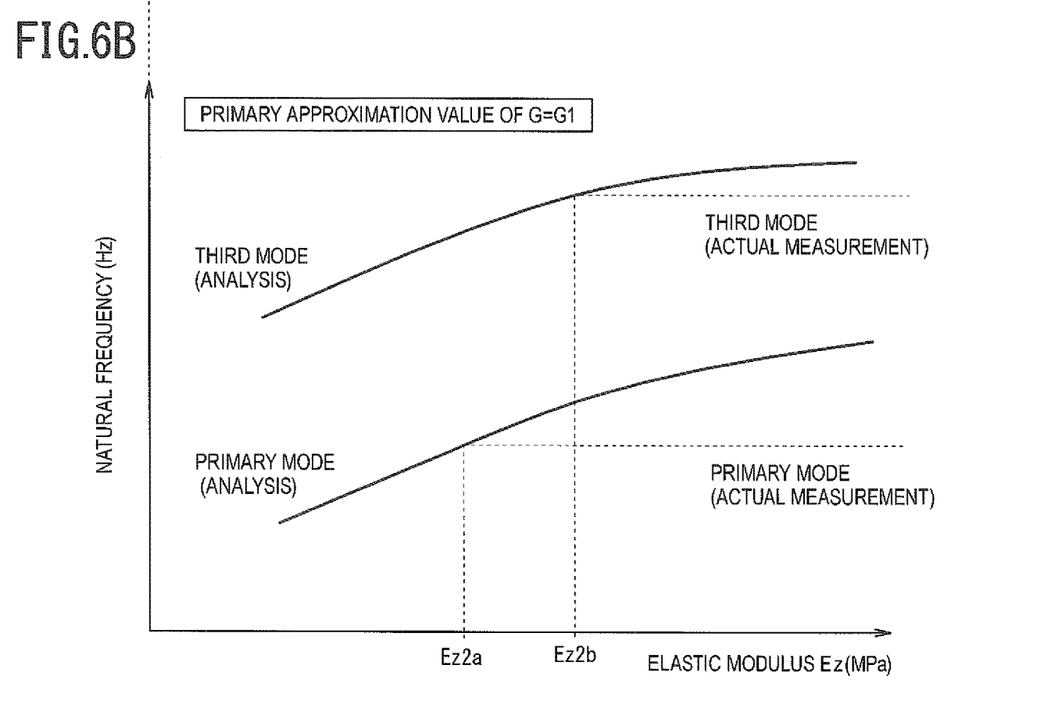

Next, a secondary approximation value of the elastic modulus Ez is obtained by using the primary approximation value G1 of the shear modulus G obtained in step S4. This is the same as the case where the approximation value of the shear modulus G is obtained. Based on the result of performing the structural analysis plurality times while changing a value by taking, as a parameter, the elastic modulus Ez, with the shear modulus G being a primary approximation value G1, a relationship between the elastic modulus Ez and the natural frequency is measured, and a characteristic diagram illustrated in FIG. 6B is created. The actual measurement values of the natural frequencies in the primary mode and the third mode are given to the characteristic diagram of FIG. 6B, and a secondary approximation value of the elastic modulus Ez can be determined (step S5).

For example, an average value of the elastic moduli Ez2a and Ez2b in the primary mode and the third mode can be set to a secondary approximation value Ez2 (Ez2=(Ez2a+Ez2b)/2) of the elastic modulus Ez.

Then, operations of determining a (n+1)th order approximation value of the shear modulus G using the nth order approximation value of the elastic modulus Ez determined in step S5 as the elastic modulus Ez of the structural analysis in step S4, and determining a (n+2)th order approximation value of the elastic modulus Ez in step S5 using the determined (n+1)th order approximation value of the shear modulus G are repeated. Therefore, since the measurement value of the natural frequency is invariable, the elastic modulus Ez and the shear modulus G that coincide with or substantially coincide with the actual measurement values of the natural frequencies in the primary mode and the third mode can be determined (step S6).

Next, the natural vibration analysis of the iron core of the 3-phase and 3-leg transformer having the shape illustrated in FIG. 2 is performed by using the structural analysis software installed in the vibration analysis device 10 (step S7). Among the mechanical elastic moduli of the iron core of the 3-phase and 3-leg transformer, the elastic modulus Ez, and the shear moduli Gyz and Gzx are values determined by the elastic matrix determination method described above. Other values of the mechanical elastic moduli are calculated by incorporating the mechanical elastic modulus of the grain orientated electrical steel sheet into the expression (5) described above.

Figure 5:
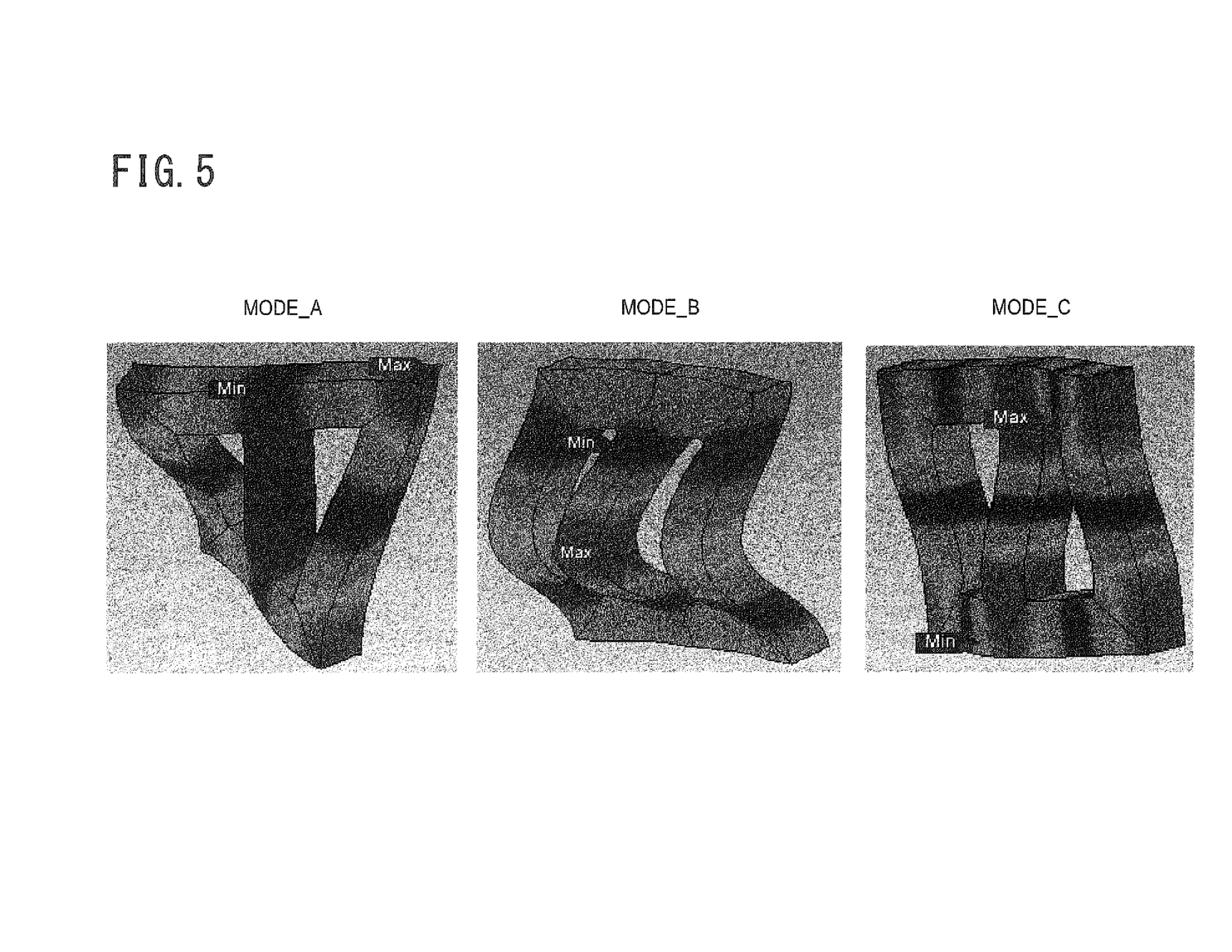
FIG. 5 is a schematic view illustrating a natural vibration mode of the iron core of the 3-phase and 3-leg transformer.

Thus, it can be seen that three natural vibration modes exist, that is, a mode A in which left and right magnetic legs are twisted in an opposite direction with respect to a center magnetic leg illustrated in FIG. 5, a mode B in which the three magnetic legs buckle, and a mode C in which an upper yoke bends backward, and a lower yoke buckles forward. The natural frequency in each mode can be calculated.

In the above description, since the natural frequency of the rectangular parallelepiped iron core for testing was measured at the center support, the natural vibration was set in the primary mode and the third mode. However, the vibration mode differs depending on the supporting method. For example, if both ends are supported, the primary mode and the secondary mode are set. Therefore, the secondary or higher order mode of the natural vibration may be appropriately selected depending on the supporting method.

In the above description, the primary approximation value of the elastic modulus Ez is assumed, and the primary approximation value of the shear modulus G is obtained from the relationship between the shear modulus G and the natural frequency, and the secondary approximation value of the elastic modulus Ez is obtained. However, it goes without saying that this order may be reversed, the primary approximation value of the shear modulus G is fixed, and the primary approximation value of the elastic modulus Ez is obtained, and the secondary approximation value of the shear modulus G may be obtained based thereon.

[Example]

First, a rectangular parallelepiped iron core for testing was manufactured by forming a same grain orientated electrical steel sheet as the grain orientated electrical steel sheet having a thickness of 0.3 mm using in iron core of the 3-phase and 3-leg transformer to be analyzed, in a rectangular shape having a width of 30 mm and a length of 280 mm, laminating 20 sheets of the grain orientated electrical steel sheets, and winding a glass tape to be fixed.

An impedance head was attached between the created rectangular parallelepiped iron core for testing and a vibrator, and the natural frequency was measured in the rectangular parallelepiped iron core for testing supported at the center. A vibration direction was the laminating direction of the steel sheets, and actually measured natural frequencies F1 and F3 in the primary and third modes of the bending vibration of the center support (both ends free) were obtained.

On the other hand, the characteristic curves illustrated in FIGS. 6A and 6B were created by setting the elastic modulus Ez of the rectangular parallelepiped iron core for testing to the elastic modulus (Ez1=220 GPa) of one steel sheet using in the rectangular parallelepiped iron core for testing, assuming the shear modulus Gyz=Gzx=As G, and performing the structural analysis plurality times while changing a value by taking, as a parameter, the shear modulus G.

Using the created characteristic curves, the primary approximation value G1 of the shear modulus G was determined from the actual measurement value F1 of the natural frequency in the primary mode and the actual measurement value F3 of the natural frequency of the third mode. In this case, G1a=0.25 and G1b=0.45. As a result, G1=0.35 [GPa] was able to be determined as a primary approximation value of the shear modulus G of the rectangular parallelepiped for testing in consideration of the slip between the grain orientated electrical steel sheets.

Next, characteristic curves (FIG. 6B) indicating the primary mode and the third mode were created by setting the primary approximation value of the shear modulus G of the rectangular parallelepiped iron core for testing to G1=0.35

[GPa], and performing the structural analysis plurality times while changing a value by taking, as a parameter, the elastic modulus Ez of the rectangular parallelepiped for testing. Ez2a=8 and Ez2b=14. Then, Ez2=11 [GPa] could be obtained as a secondary approximation value of the elastic modulus Ez of the rectangular parallelepiped for testing in consideration of slip between grain orientated electrical steel sheets.

Next, operations are repeated of setting the secondary approximation value of the elastic modulus Ez of the rectangular parallelepiped iron core for testing to Ez2=11 [GPa], determining the approximation value of the shear modulus G, and obtaining the approximation value of the elastic modulus Ez by using an approximation value of a new shear modulus G obtained here. As a result, Ez=10 [GPa] and G=0.29 [GPa] were obtained as the elastic modulus and the shear modulus in which the calculated value of the natural frequency of the rectangular parallelepiped for testing coincides with the actual measurement value of the natural frequency.

By the way, when the natural vibration analysis of the iron core of the transformer is performed, the vibration modes as illustrated in FIG. 5 appear.

Here, as in the example of the related art, the natural vibration analysis of the iron core of the 3-phase and 3-leg transformer having the shape illustrated in FIG. 2 was performed assuming that the mechanical elastic modulus of the iron core of the transformer is equal to the mechanical elastic modulus of the grain orientated electrical steel sheet. As a result, the natural frequency was 1006 Hz in the mode A and was 2004 Hz in the mode B, and no vibration mode of the mode C did not appear.

Next, after the laminated iron core 21 of the 3-phase and 3-leg transformer having the shape illustrated in FIG. 2 was actually manufactured by using a grain orientated electrical steel sheet having a sheet thickness of 0.3 mm, a measurement of the natural frequency of the iron core obtained by performing the vibration by an impact hammer was performed. As a result, the three vibration modes A, B, and C illustrated in FIG. 5 were observed, and the measured natural frequencies were 141 Hz in the mode A, 255 Hz in the mode B, and 293 Hz in the mode C.

As described above, the natural frequency obtained by the natural vibration analysis of the related art has a result that is significantly different from the actually measured natural frequency. This is considered to be due to the fact that the natural vibration analysis of the related art does not consider the slip between the laminated steel sheets based on the shear modulus of the two surfaces including the laminating direction of the laminated iron core.

Therefore, the shear modulus of the 3-phase and 3-leg transformer was set to G=0.29 [GPa], which is a value determined by the elastic matrix determination method described above, the elastic modulus was set to Ez=10 [GPa], and then the vibration analysis was performed by using the vibration analysis device 10. As a result, the natural frequencies in the mode A illustrated in FIG. 5 was 166 Hz, the mode B was 207 Hz, and the mode C was 355 Hz. These values much better coincide with the measured value of the natural frequency when compared to the results by the analysis method of the related art.

From the above results, the shear modulus Gyz=Gzx=G in the elastic matrix [C] was determined by the elastic matrix determination method according to the present embodiment, the determined shear modulus Gyz=Gzx=G was incorporated in the configuration expression (3) described above, and the natural vibration analysis was performed. Therefore, it could be found that the vibration characteristics can be calculated with higher accuracy compared to those by the method of the related art.

As described above, according to the present embodiment, the natural vibration analysis is performed plurality times by using the iron core for testing by taking as a parameter, the shear modulus Gyz=Gzx=G. Therefore, it is possible to set the value of the shear modulus Gyz=Gzx=G in consideration of the slip between the laminated grain orientated electrical steel sheets. Therefore, the vibration characteristics of the laminated iron core can be calculated with high accuracy by incorporating the determined shear modulus into the elastic matrix and performing the vibration analysis.

Therefore, when the iron core of the 3-phase and 3-leg transformer is designed by using various electrical steel sheets, the iron core for testing is manufactured by using the same electrical steel sheet, and this iron core for testing is used to determine the elastic modulus Ez and the shear modulus Gyz=Gzx=G. Therefore, it is possible to determine an appropriate elastic matrix, that is, a response function in consideration of the slip between the laminated steel sheets.

Also, by incorporating the determined shear modulus Gyz=Gzx=G into the elastic matrix and performing natural vibration analysis, the natural frequency in each vibration mode of the iron core of the 3-phase and 3-leg transformer can be calculated with high accuracy.

In the embodiment described above, a case is described where the operations of alternately and sequentially determining the approximation values of the elastic modulus Ez and the shear modulus Gyz=Gzx=G for the iron core for testing, and thereby the final values of Ez and G are determined. However, the present invention is not limited to this, and a method may be provided, in which a three-dimensional map of the elastic modulus Ez and the shear modulus G with respect to the natural frequency is created by performing the natural vibration analysis plurality times. Therefore, the natural frequency calculation value of the iron core for testing coincides with the actual measurement value of the natural frequency by taking, as parameters, the elastic modulus Ez and the shear modulus Gyz=Gzx=G, and the elastic modulus Ez and the shear modulus G corresponding to the actual measurement value of the natural frequency are determined from the three-dimensional map.

As a result, by using the iron core for testing, the elastic modulus Ez and the shear modulus G that can obtain the calculated value of the natural frequency close to the actual measurement value of the natural frequency can be determined.

Therefore, by incorporating the determined elastic modulus Ez and shear modulus G into a stress-strain configuration expression and performing natural vibration analysis of the laminated iron core such as an iron core of the 3-phase and 3-leg transformer, more accurate natural vibration analysis can be performed.

Further, in the embodiment described above, the case where the rectangular parallelepiped iron core is used as the iron core for testing has been described. However, the present invention is not limited to this, and the iron core of the 3-phase and 3-leg transformer for testing is manufactured, and the shear modulus Gyz=Gzx=G or the elastic modulus Ez, and the shear modulus Gyz=Gzx=G, in which the natural frequency coincides with the measurement value, may be determined for the iron core of the 3-phase and 3-leg transformer for testing.

Further, in the embodiment described above, the case where the vibration analysis is performed by using the relational expression of the stress and the strain using the elastic matrix [C] that is the stiffness matrix as the response function has been described. However, the present invention is not limited to this, and the vibration analysis may be performed by using a relational expression $\{\varepsilon\}=[S]\{\sigma\}$ of strain and stress using the compliance matrix [S] as the response function. In this case, $S_{44}=1/Gyz$, $S_{55}=1/Gzx$, and $S_{66}=1/Gzy$.

Further, in the embodiment described above, the vibration analysis of the 3-phase and 3-leg transformer has been described. However, the present invention is not limited to this, and the present invention is also applicable to a vibration analysis of a laminated iron core in a three-phase and five-leg transformer and other transformers.

REFERENCE SIGNS LIST 10 vibration analysis device
11 CPU
12 computation processing device
13 internal bus
14 internal storage device
15 external storage device
16 input device
17 output device
18 recording medium
21 laminated iron core
22 electrical steel sheet
22a upper yoke
22b lower yoke
22c leg

The invention claimed is:

1. An elastic matrix determination method for a laminated iron core obtained by laminating steel sheets in a laminating direction, the method comprising:
   creating an iron core for testing obtained by laminating steel sheets each using a same steel sheets as the laminated iron core in the laminating direction;
   supporting a center of the created iron core for testing, and measuring an actual measurement value of a natural frequency by vibrating the created iron core for testing in the laminating direction;
   estimating a relationship between a shear modulus in two planes of the iron core for testing and the natural frequency by performing a structural analysis plurality times using structural analysis software for the iron core for testing, the two planes being orthogonal to each other and extending in the laminating direction; and
   determining the shear modulus from a relationship between the shear modulus and the natural frequency estimated by using the actual measurement value of the natural frequency.

2. The elastic matrix determination method according to claim 1, wherein the laminated iron core is configured by laminating a plurality of electrical steel sheets.

3. The elastic matrix determination method according to claim 2, wherein the laminated iron core is a laminated iron core for a transformer.

4. A vibration analysis method for a laminated iron core obtained by laminating steel sheets, the method comprising:
   performing a vibration analysis of a laminated iron core by incorporating a shear modulus determined by the elastic matrix determination method according to claim 1 into an elastic matrix of a configuration expression in which a relationship between stress and strain is expressed by a tensor display using a response function.

5. The vibration analysis method for a laminated iron core according to claim 4, wherein the laminated iron core is an iron core for a transformer, obtained by laminating a plurality of electrical steel sheets.

6. The elastic matrix determination method according to claim 1, wherein the iron core for testing is a rectangular parallelepiped.

7. The elastic matrix determination method according to claim 1, wherein the structural analysis is performed by taking, as a parameter, the shear modulus.

8. An elastic matrix determination method for a laminated iron core obtained by laminating steel sheets in a laminating direction, the method comprising:
   forming an iron core for testing obtained by laminating steel sheets each using a same steel sheets as the laminated iron core in the laminating direction, and measuring an actual measurement value of a natural frequency by vibrating the iron core for testing in the laminating direction;
   measuring a relationship between a shear modulus in two planes of the iron core for testing, an elastic modulus, and the natural frequency by performing a structural analysis plurality times, for the iron core for testing, the two planes being orthogonal to each other and extending in the laminating direction; and
   determining the shear modulus and the elastic modulus from a relationship between the shear modulus, the elastic modulus, and the natural frequency measured by using the actual measurement value of the natural frequency.

9. A vibration analysis method for a laminated iron core obtained by laminating steel sheets, the method comprising:
   performing a vibration analysis of a laminated iron core by incorporating a shear modulus and an elastic modulus determined by the elastic matrix determination method according to claim 8 into an elastic matrix of a configuration expression in which a relationship between stress and strain is expressed by a tensor display using a response function.

10. The vibration analysis method for a laminated iron core according to claim 9, wherein the laminated iron core is an iron core for a transformer, obtained by laminating a plurality of electrical steel sheets.

11. The elastic matrix determination method according to claim 8, wherein the laminated iron core is configured by laminating a plurality of electrical steel sheets.

12. The elastic matrix determination method according to claim 8, wherein the structural analysis is performed by taking, as individual parameters, the shear modulus and the elastic modulus.

* * * * *